US006911342B2

(12) United States Patent
Helenek et al.

(10) Patent No.: US 6,911,342 B2
(45) Date of Patent: Jun. 28, 2005

(54) BIOEQUIVALENCE TEST FOR IRON-CONTAINING FORMULATIONS

(75) Inventors: Mary Jane Helenek, Brookville, NY (US); Ralf A. Lange, Amagansett, NY (US); Richard P. Lawrence, Calverton, NY (US)

(73) Assignee: Luitpold Pharmaceuticals, Inc., Shirley, NY (US)

( * ) Notice: Subject to any disclaimer, the term of this patent is extended or adjusted under 35 U.S.C. 154(b) by 247 days.

(21) Appl. No.: 10/227,445

(22) Filed: Aug. 26, 2002

(65) Prior Publication Data

US 2004/0038416 A1 Feb. 26, 2004

(51) Int. Cl.$^7$ ............................................. G01N 33/20
(52) U.S. Cl. ............................ 436/84; 436/73; 436/93; 436/94
(58) Field of Search ............................ 436/73, 74, 84, 436/93, 94, 904; 422/61

(56) References Cited

U.S. PATENT DOCUMENTS 5,624,668 A    4/1997   Lawrence et al.

FOREIGN PATENT DOCUMENTS

WO   WO 97/11711   4/1997

OTHER PUBLICATIONS

"USP Monograph for Iron Sucrose Injection", 2nd Supplement to the USP–NF, pp. 1–5, Jul./Aug. 2002.

"Guidance for Industry, Dissolution Testing of Immediate Release Solid Oral Dosage Forms", U.S. Dept. of Health and Human Services, Food & Drug Administration, CDER, Aug. 1997.

S. Beshara, et al., "Kinetic analysis of 52Fe–labelled iron(III) hydroxide–sucrose complex following bolus administration using positron emission tomography", *Br J Haematol*, vol. 104 (2), pp. 288–295, Feb. 1999.

Richard Lawrence, "Development and Comparison of Iron Dextran Products", *PDA Journal of Pharmaceutical Science & Technology*, vol. 52, No. 5, pp. 190–197, Sep./Oct. 1998.

U, Erni, et al., "Chemical Characterization of Iron (III)–Hydroxide–Dextrin Complexes", Arzheim.–Forsch./Drug. Res., vol. 34, (II), pp. 1555–1559, (1984).

*Primary Examiner*—Maureen M. Wallenhorst
(74) *Attorney, Agent, or Firm*—Morgan Lewis & Bockius LLP

(57) ABSTRACT

A rapid method for assessing the bioequivalence of iron in iron-supplement formulations, particularly iron-sucrose formulations is described, which is based upon the kinetics of reduction of iron (III) to iron (II) in a sample of the formulation. Quality control methods and associated kits also are described.

25 Claims, 1 Drawing Sheet

BIOEQUIVALENCE TEST FOR IRON-CONTAINING FORMULATIONS

FIELD OF THE INVENTION

The invention relates to a rapid method for assessing the bioequivalence of iron in iron supplement formulations, particularly iron-carbohydrate complexes, based upon the reduction kinetics of iron (III) to iron (II) in a sample of the formulation. The invention also relates to quality control methods and associated kits.

BACKGROUND OF THE INVENTION

Iron dextran was developed for the treatment of iron deficiency conditions, and originally was administered by intramuscular injection to iron deficiency anemia patients who could not tolerate various formulations of oral iron salts. See, e.g., Lawrence, "Development and Comparison of Iron Dextran Products," *PDA Journal of Pharmaceutical Science & Technology* 52(5):190–197 (1998). Subsequently, iron dextran was also administered intravenously and found to produce a similar beneficial outcome.

A variety of iron-containing formulations have been developed. Intravenous injections of colloidal ferric hydroxide preparations, particularly iron sucrose, are clinically indicated for the treatment of iron deficiency anemia in patients undergoing chronic hemodialysis who are receiving supplemental erythropoietin therapy.

Iron sucrose is formulated as a colloidal suspension and administered as a prodrug that is taken up by cells of the reticuloendothelial system, which release ionic iron. The ionic iron binds to transferrin, which, in turn, transfers it to the bone marrow for erythropoiesis or to ferritin and the iron storage pool in the marrow, spleen and liver.

Physiology and Metabolism of Iron

The human body stores trivalent iron as ferritin and hemosiderin. Ferritin is comprised of an outer protein shell containing a storage cavity for a polynuclear ferric hydroxide/phosphate core of approximate composition $[(FeOOH)_8(Fe)—OPO_3H_2)]_n$. Ferritin's protein shell, apoferritin, is composed of 24 polypeptide subunits forming the apoferritin molecule, which has an average molecular weight of about 440,000. Apoferritin's outer shell has a diameter of approximately 13 nanometers (130 Å) with an interior cavity of about 7 nanometers (70 Å).

Ferritin's protein shell, apoferritin, functions as a ferroxidase enzyme in the binding and oxidizing of divalent iron which it then stores within its cavity as a polynuclear ferric hydroxide/phosphate core. Ferritin may contain up to 4,500 polymerized ferric ions with a molecular weight for the entire molecule ranging from 700,000 to 800,000. Over 30% of the weight of the ferritin molecule may be iron.

When the amount of available iron exceeds ferritin's iron storage mechanism, an aggregated ferritin is formed called hemosiderin, which is a normal constituent of the monocyte-macrophage system. Hemosiderin is composed of molecules of ferritin, which have lost part of their protein shell and become aggregated. Hemosiderin accounts for about one third of normal iron stores and accumulates as insoluble granules in the cells of the reticuloendothelial system.

Ferritin is water soluble and may enter the blood stream through osmosis. Normal serum levels of ferritin are dependent on sex/age and range between 40 and 160 ng/mL. It is believed that in the blood stream, ferritin slowly releases divalent iron in conjunction with a reducing agent, such as reduced flavin mononucleotide and to a lesser extent, ascorbic acid. The divalent iron is oxidized back to trivalent iron by ceruloplasmin, then tightly bound to the blood protein apotransferrin forming transferrin. The molecular weight of transferrin is about 76,000 and each molecule has two binding sites for ferric ions.

Upon administration to a patient, an iron sucrose complex (or other trivalent iron colloids formulated, e.g., with gluconate, dextran, sorbitol or dextrin) is removed from the blood stream as a particle by the macrophages of the reticuloendothelial system and metabolized to replenish the body's iron stores of hemosiderin, ferritin and transferrin. The rate of removal from the blood stream is dependent on both the colloidal ferric hydroxide's particle size and composition.

Synthesis of Iron Carbohydrate Complexes

Iron carbohydrate complexes, such as iron sucrose, are composed of colloidal ferric hydroxide particles (i.e., cores) in complex with sucrose. These iron cores are prepared by the neutralization of ferric chloride with an alkali to a pH of 2. At this pH, the saturation of hydroxide ions induces the formation of colloidal ferric hydroxide, which after formation complexes in situ with a suitable carbohydrate, such as sucrose. The structure of the iron core follows classic coordination chemistry. The carbohydrate complexes with the iron core as its hydroxyl groups displace the water molecules bonded to the iron core's outer surface.

The bonding between the iron core and the carbohydrate is a non-covalent intermolecular force, such as the attraction of partial positive charges of the core's surface iron atoms to the negative dipole moments of the carbohydrate's hydroxyl groups.

Iron sucrose, for example, has a molecular weight ($M_w$) of about 34,000–60,000 Daltons and a molecular formula as follows:

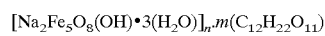

where n is the degree of iron polymerization and m is the number of sucrose molecules ($C_{12}H_{22}O_{11}$) in complex with the poly-nuclear polymerized iron core:

In solution, an equilibrium exists between a poly-nuclear polymerized iron core (Pn) and its solubilizing ligand (L):

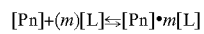

In order to assure a stable water-soluble iron complex, an excess amount of the solubilizing ligand is required and the equilibrium is as follows:

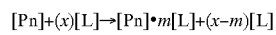

A preferred method of synthesizing such iron carbohydrate complexes is described, for example, in published PCT Application WO 97/11711 (1997) by Lawrence et al.

Evaluation of Iron Carbohydrate Homogeneity

Iron dextran complexes produced by the neutralization of ferric chloride in the presence of dextran have a similar structural formula, but differ in the degree of polymerization of the ferric hydroxide cores. See, for example, Lawrence (1998). The Lawrence paper also discusses methods to assess the homogeneity of particle sizes in an iron dextran complex by evaluating reduction degradation kinetics. After describing the evaluation of three iron dextran products from different manufacturers, the paper reports that there were marked differences among them in each of the physical and chemical parameters measured.

Determination of Bioequivalence of Iron Dextran Particles

As noted above, commercial iron supplement formulations are complex colloidal suspensions. For example, according to the USP Monograph for Iron Sucrose Injection by Luitpold Pharmaceuticals, Inc., to be published in the 2nd Supplement to the USP 25 in July/August 2002, such a formulation is pH controlled, and contains a controlled amount of particulate matter in addition to the iron and sucrose components. A comparison between commercial preparations of iron (III) dextrin complexes was reported by Erni, et al., "Chemical Characterization of Iron (III)-Hydroxide-Dextrin Complexes" *Arzneim.-Forsch./Drug Res.* 34(11):1555–1559 (1984). The paper noted that hydrolysis products of iron (III) may differ enormously in their structural, morphological, and chemical properties depending on the conditions under which they are formed and other factors. Attention was drawn to the nature of such hydrolysis products rather than the oxidation state of the iron—that is, iron (II) as compared with iron (III).

Erni et al. discusses the kinetic analysis of iron (III) reduction and relates it to the distribution of particle sizes and a range of surface to volume ratios in monodisperse as compared with polydisperse systems. See, for example, Sections 2.3 and 3.2 at pages 1556–57. Ascorbic acid, citric acid, phosphoric acid and sorbitol are a few of the reducing agents utilized by Erni, et al. Bioavailability in the context of oral preparations is also discussed; however, notably, these authors conclude that chemical tests alone will not allow for the prediction of bioavailability because they do not simulate the complex chemical environment of the intestine (See page 1559).

Other known processes have utilized the molecular weight distribution of a complex to correlate its bioavailability. However, this kind of distribution appears to vary dependent on the method, protocol and standards used in the molecular weight analysis. See, for instance, PCT WO97/11711 to Lawrence, et al.

General guidance on in vitro testing for immediate release solid oral dosage forms by dissolution testing is provided by the FDA at http://www.fda.gov/cder/guidance/1713bp1.pdf, and is entitled "Guidance for Industry: Dissolution Testing of Intermediate Release Solid Oral Dosage Forms."

Thus, while an evaluation of the particle size distribution of iron-containing complexes has been reported, based upon their reduction degradation kinetics, the literature does not appear to have identified any particular correlation between the distribution of particle size and bioequivalence. Indeed, specific kinetic parameters, such as $T_{75}$, have not heretofore been defined and associated with bioequivalence. What has been needed, therefore, is an accurate, inexpensive method for measuring reliably and consistently the bioequivalence of iron-containing compositions, as well as a quality control standard for so doing. Such a method would also permit the optimization of iron supplement formulations and the comparison of batches in production.

SUMMARY OF THE INVENTION

Figure 1:
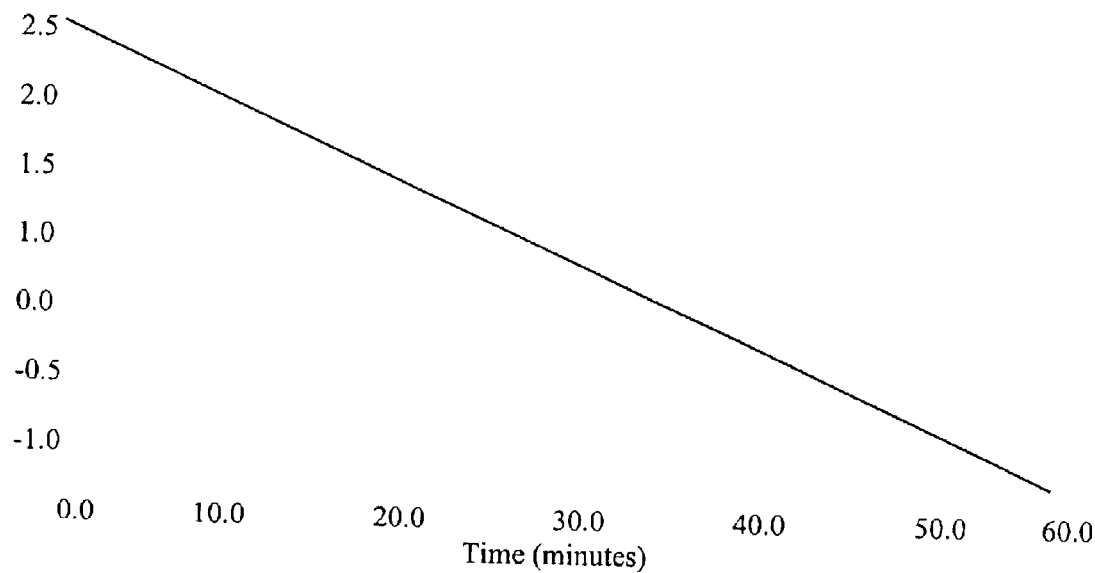
FIG. 1 depicts graphs of the log (% trivalent iron concentration) vs. time.
Figure 1:
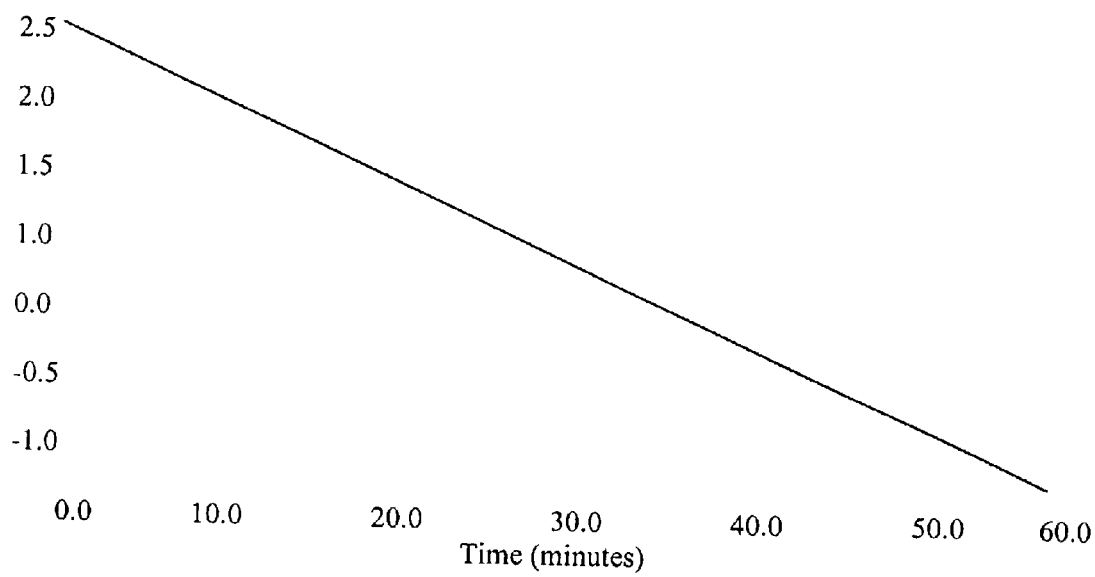

In the human body, the metabolism and mobilization of iron involve a series of oxidation/reduction reactions wherein the valence of the iron changes back and forth from its divalent and trivalent states. In order to control and monitor the batch-to-batch bioequivalence of iron-sucrose complexes, an in vitro test has been developed to measure the colloidal ferric hydroxide's rate of reduction from trivalent iron to divalent iron. The colloidal ferric hydroxide core dissociates as the iron is reduced, and the rate of dissociation of the colloidal ferric hydroxide core is directly proportional to its particle size. In addition, for ferric hydroxide cores that are uniform in particle size (i.e., monodispersed) and composition, their rate of reduction follows first order kinetics.

In a preferred embodiment of the present invention, ascorbic acid, added in excess, in physiological saline is used as the in vitro test's reducing agent. The ascorbic acid ($C_6H_8O_6$) reduces the iron core's trivalent iron ($Fe^{3+}$) to the divalent iron ($Fe^{2+}$) ion as follows:

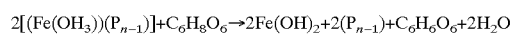

$$2[(Fe(OH)_3))(P_{n-1})] + C_6H_8O_6 \rightarrow 2Fe(OH)_2 + 2(P_{n-1}) + C_6H_6O_6 + 2H_2O$$

Ascorbic acid is oxidized to dehydroascorbic acid ($C_6H_6O_6$) and ferric hydroxide ($Fe(OH)_3$) is reduced to ferrous hydroxide ($Fe(OH)_2$).

The colloidal ferric hydroxide complexes are dark red to brown solutions with a strong adsorption band at 450 nm. As the reduction to ferrous hydroxide occurs, the color is discharged, resulting in a decrease in absorbency. This decay (or dissociation) can be easily monitored in a temperature controlled (37±1° C.) UV/Vis spectrophotometer set at 450 nm.

In another embodiment of the present invention, the $T_{75}$ time for the reduction of the iron-carbohydrate complex is used to determined the relative bioequivalence by reducing the complex with an appropriate reducing agent. A preferred bioequivalence standard for an iron-sucrose formulation is met if its $T_{75}$ reduction time is not more than 20 minutes and its reduction reaction plot of "Log (% Trivalent Iron Concentration)" versus "Time" is linear with a correlation coefficient absolute value of not less than 0.98.

Additional features, advantages, and embodiments of the invention may be set forth or apparent from consideration of the following detailed description and claims. Moreover, it is to be understood that both the foregoing summary of the invention and the following detailed description are exemplary and intended to provide further explanation without limiting the scope of the invention as claimed.

DETAILED DESCRIPTION OF THE INVENTION

The present invention is based, in part, on the discovery that the bioequivalence of iron in iron-carbohydrate complexes, particularly iron-sucrose formulations, may usefully be determined by assessing the kinetics of reduction degradation of the iron (III) containing complexes. Specifically, the present inventors have discovered that the reduction time for a given preparation can be usefully correlated with bioequivalence. Since the kinetics of reduction are a function of the particle size distribution of the complexes, an analysis of these kinetics allows a determination of the particle size distribution. The particle size distribution is used, in turn, to determine the bioequivalence. This method reduces the analysis time and significantly reduces the costs otherwise associated with the evaluation of bioequivalence of iron supplement formulations during and after their production.

The present invention is directed to a method of determining the relative bioequivalence of iron in an iron-carbohydrate complex by contacting the complex with a reducing agent, determining the reduction kinetics of the complex, and comparing these kinetics to the reduction kinetics of a standard composition of known bioequivalence.

The present invention also includes a method of determining the relative bioequivalence of iron in an iron-carbohydrate complex by contacting the complex with a reducing agent and determining a $T_{75}$ for the reduction kinetics of the complex. A $T_{75}$ of less than about 20 minutes indicates an effective bioequivalence of iron in the complex when administered to a subject. Preferably the $T_{75}$ is less than about 18 minutes, and more preferably the $T_{75}$ is between about 9 to about 18 minutes.

Preferably the iron-carbohydrate complexes are made up of carbohydrates, such as dextran, dextrin, gluconate, sorbitol and sucrose, for example. Most preferably, the iron-carbohydrate complex is iron-sucrose.

The inventive methods may utilize any number of suitable reducing agents including, for instance, reduced flavin mononucleotide, dithionite, thioglycolate, hydroquinone, lactate, citrate, bicarbonate, pyruvate, succinate, fructose, cysteine, sorbitol, and especially preferred is ascorbic acid. The reducing agent may be present in an amount sufficient to drive the reduction reaction to completion, or at least to substantial completion, and preferably, in about a 50-fold excess to the iron-carbohydrate complex. Also preferred is use of a reducing agent that is in solution and has an acidic pH, most preferably, the solution pH is from about 1.0 to about 4.0.

The present invention also includes an inventive quality control apparatus for determining the bioequivalence of iron-carbohydrate complexes. The inventive apparatus features a computer-monitored production system which monitors the reduction kinetics of the product of a reaction between a colloidal ferric hydroxide and a carbohydrate at different stages of the reaction.

Preferably, the product is reduced with a reducing agent, such as ascorbic acid. Preferably, the reducing agent is present in an amount sufficient to drive the reduction reaction to completion, or at least to substantial completion. More preferably, the reducing agent is present in at least about a 50-fold excess to the product. Also preferred is a reducing agent that is in solution and has an acidic pH, especially preferred is a solution pH of from about 1.0 to about 4.0.

The product is, preferably, a complex of iron and a carbohydrate selected from the group consisting of dextran, dextrin, gluconate, sorbitol and sucrose. Particularly, preferred is when the carbohydrate is sucrose.

The present invention is also directed to a quality control method to identify batches of iron-carbohydrate complexes having substantially the same bioequivalence. The method includes formulating iron-carbohydrate complexes, using the above method to determine the reduction kinetics of a selected batch of iron-carbohydrate complex, and identifying batches of iron-carbohydrate complex that meet the reduction kinetics of a standard composition of known bioequivalence.

A kit for assessing the bioequivalence of an iron-sucrose complex utilizing a container to hold a sample of the iron-sucrose complex, means for determining the reduction kinetics of the iron-sucrose complex, and means for relating the reduction kinetics to the bioequivalence of a known standard iron-sucrose complex is also included in the present invention.

Definitions

"Bioavailability" means the physiological availability of a given amount of the active component of a drug administered orally to a subject, as distinct from the drug's chemical concentration or potency.

"Bioequivalence" means a substantially similar activity profile of a drug as compared with a standard, or another formulation, for that drug or another drug.

"$T_{75}$" or "$T_{75}$ interval" or "$T_{75}$ reduction time" means the time (in minutes) at which not less than 75% of iron sucrose solution's colloidal ferric hydroxide is reduced (i.e., dissociated).

In light of the foregoing discussion, the specific examples presented below are illustrative only and are not intended to limit the scope of the invention. Other generic and specific configurations will be apparent to persons skilled in the art.

EXAMPLES

Stock solutions are prepared daily. A 0.9% sodium chloride diluting solution (solution A) is prepared by weighing 9.00 g of sodium chloride into a 1000 mL volumetric flask and adding purified water to volume. The solution is then maintained at 37° C. in a water bath.

A stock ascorbic acid solution (solution B) is prepared by weighing about 8.8 g into a 50 mL volumetric flask, and then add as much as necessary of solution A. This solution is also maintained at 37° C.

An iron sucrose stock solution is prepared by transferring 5.0 mL of the sample to a 50 mL volumetric flask, and then adding purified water to volume. This solution is also maintained at 37° C.

The general procedure to monitor the reaction is to place 20.0 mL of solution A, 4.0 mL of solution B and 1.0 mL of iron sucrose stock solution in a 25 mL volumetric flask. This solution is mixed well and then an appropriate amount is transferred to a 1 cm quartz cell in a temperature controlled UV/Vis spectrophotometer set at 37° C. The absorption at 450 nm is measured at 1-minute intervals for a total reaction time of 80 minutes. Solution A is used as the blank.

The percentage of trivalent iron concentration at a given observation time is calculated using the following equation:

$$100 \times [(\text{Observed Abs.} - \text{Final Abs.})/(\text{Initial Abs.} - \text{Final Abs.})]$$

The iron sucrose solution meets its bioequivalence standard if the $T_{75}$ reduction time is not more than 20 minutes and a plot of "Log(% Trivalent Iron Concentration)" versus "Time" over 60 minutes is linear with a correlation coefficient of not less than 0.98.

Example 1

In Vitro Test's Use in Control of Intermediate Iron Sucrose Solutions

A saturated ferric chloride solution is contacted with a 10% w/v sodium carbonate solution at a neutral pH of about 7. The resulting colloidal ferric hydroxide gel is washed with sufficient quantities of purified water to remove all trace amounts of sodium chloride, present as a by-product of the reaction.

A sufficient quantity of saturated sucrose solution is added to the colloidal ferric hydroxide gel at a volume equivalent to produce a final solution containing approximately 4.0% w/w elemental iron. The solution's pH is adjusted to 10.7 with sodium hydroxide and the solution is mixed at 90° C. for 36 hours. In-process QC samples are taken for pH, iron content and in vitro bioequivalence testing. If the results are within limits, the solution's volume is adjusted by addition of purified water to provide a final iron content of about 4.0% w/w elemental iron, then filtered through a 0.2 micron membrane.

The following in vitro test results were obtained on an intermediate iron sucrose solution containing 3.7% w/w elemental iron:

TABLE 1

In Vitro Testing of Intermediate Iron Sucrose Solution

| Time (Minutes) | Abs. at 450 nm | LOG (% Trivalent Iron Conc.) |
|---|---|---|
| 0.0 | 1.5154 | 2.000 |
| 5.0 | 0.9493 | 1.792 |
| 10.0 | 0.5762 | 1.568 |
| 15.0 | 0.3369 | 1.320 |
| 20.0 | 0.2012 | 1.071 |
| 25.0 | 0.1312 | 0.849 |
| 30.0 | 0.0934 | 0.656 |
| 35.0 | 0.0708 | 0.479 |
| 40.0 | 0.0565 | 0.313 |
| 45.0 | 0.0463 | 0.137 |
| 50.0 | 0.0402 | −0.018 |
| 55.0 | 0.0348 | −0.224 |
| 60.0 | 0.0315 | −0.425 |
| 65.0 | 0.0292 | — |
| 70.0 | 0.0276 | — |
| 75.0 | 0.0267 | — |
| 80.0 | 0.0259 | — |

| Regression output: | Constant (b): | 1.93237 |
|---|---|---|
| | Std Err of Y Est: | 0.05684 |
| | R Squared: | 0.99514 |
| | Correlation Coefficient: | 0.99757 |
| | No. of Observations: | 13 |
| | Degrees of Freedom: | 11 |
| | X Coefficient (m): | −0.04001 |
| | Std Err of Coef.: | 0.00084 |

The regression output for Graph 1 demonstrates that the trivalent iron's reduction is linear with a correlation coefficient of 0.99757. This indicates that the reduction of this intermediate iron sucrose solution's colloidal ferric hydroxide cores follows first order kinetics, where the $T_{75}$ is calculated using the following equation:

$$T_{75} = (1.3979 - b)/m$$

Where: "1.3979" is the Log of the % trivalent iron concentration at the 75% reduction time point (i.e., % trivalent iron concentration=25%), "b" is the constant, and "m" is the X Coefficient.

Using the values of "b" and "m" obtained from the linear regression of Graph 1, the $T_{75}$ for this intermediate iron sucrose solution is found at 13.36 minutes.

Example 2
In Vitro Test's Use in Control of Iron Sucrose Solutions Suitable for Injectable Use An iron sucrose solution, suitable for injectable use, is prepared by diluting an intermediate solution, as described in Example 1, with water for injection to a final elemental iron concentration of 20 mg/mL. The resulting solution's pH is adjusted to 10.8 with sodium hydroxide, then mixed until homogeneous. The solution is transferred via stainless steel supply lines and filtered through two sterilized 0.2 micron filters set-up in series into a sterilized filling flask. The filter and filling flask are set-up under laminar flow inside the designated filling room under constant class 100 conditions.

All equipment used during filling is identified, sterilized, and recorded. Stoppers are washed, siliconized, depyrogenated and sterilized. The glassware is washed using deionized water with a final rinse of water for injection, then depyrogenated.

The vial fillers are situated under laminar flow class 100 work stations in environmentally controlled class 10,000 clean rooms. HEPA filters directly above the vial fillers provide an invisible wall of sterile particle-free air to prevent contamination. After filling is completed, the product is heat treated in an autoclave at 100° C. for 35 minutes.

The following in vitro test results were obtained on an iron sucrose solution, suitable for injectable use, containing 20 mg/mL elemental iron:

TABLE 2

In Vitro Testing of Injectable Iron Sucrose Solution

| Time (minutes) | Abs at 450 nm | Log (% Trivalent Iron Conc.) |
|---|---|---|
| 0.0 | 0.9735 | 2.000 |
| 5.0 | 0.5382 | 1.735 |
| 10.0 | 0.2859 | 1.444 |
| 15.0 | 0.1650 | 1.179 |
| 20.0 | 0.1050 | 0.944 |
| 25.0 | 0.0745 | 0.748 |
| 30.0 | 0.0552 | 0.553 |
| 35.0 | 0.0432 | 0.364 |
| 40.0 | 0.0351 | 0.164 |
| 45.0 | 0.0314 | 0.030 |
| 50.0 | 0.0270 | −0.215 |
| 55.0 | 0.0250 | −0.399 |
| 60.0 | 0.0235 | −0.617 |
| 65.0 | 0.0220 | — |
| 70.0 | 0.0215 | — |
| 75.0 | 0.0207 | — |
| 80.0 | 0.0212 | — |

| Regression output: | Constant: | 1.87588 |
|---|---|---|
| | Std Err of Y Est: | 0.06695 |
| | R Squared: | 0.99395 |
| | Correlation Coefficient: | 0.99697 |
| | No. of Observations: | 13 |
| | Degrees of Freedom: | 11 |
| | X Coefficient: | −0.0422 |
| | Std Err of Coef.: | 0.00099 |

As with example 1, the regression output for Graph 2 demonstrates that the trivalent iron's reduction is linear with a correlation coefficient of 0.9969, indicating that the reduction of this iron sucrose solution, suitable for injectable use, follows first order kinetics. The $T_{75}$ calculated using the following equation:

$$T_{75} = (1.3979 - b)/m;$$

is found at 11.32 minutes.

Although the present invention has been described in detail with reference to examples above, it is understood that the various modifications can be made without departing from the spirit of the invention. Accordingly, the invention is limited only by the following claims. All cited patents and publications referred to in this application are herein incorporated by reference in their entirety.

We claim the following:

1. A method of assessing bioequivalence of iron colloids in an iron-carbohydrate complex for administering to a subject, comprising:
    contacting the complex with a reducing agent;
    determining a $T_{75}$ for the reduction kinetics of the complex; wherein a $T_{75}$ of less than about 20 minutes indicates an effective bioequivalence of iron in the complex when administered to a subject.

2. The method according to claim 1, wherein the carbohydrate of the iron-carbohydrate complex comprises at least one member selected from the group consisting of dextran, dextrin, gluconate, sorbitol and sucrose.

3. The method according to claim 2, wherein the carbohydrate comprises sucrose.

4. The method according to claim 1, wherein the reducing agent comprises at least one member selected from the group consisting of reduced flavin mononucleotide, dithionite, thioglycolate, hydroquinone, lactate, citrate, bicarbonate, pyruvate, succinate, fructose, cysteine, sorbitol, and ascorbic acid.

5. The method according to claim 4, wherein the reducing agent comprises ascorbic acid.

6. The method according to claim 1, wherein the reducing agent is presented in an amount sufficient to drive the reduction of the complex to substantial completion.

7. The method according to claim 1, wherein the reducing agent is present in at least about a 50-fold excess to the iron-carbohydrate complex.

8. The method according to claim 1, wherein the reducing agent is in solution and has an acidic pH.

9. The method according to claim 8, wherein the solution has a pH of from about 1.0 to about 4.0.

10. A quality control method to identify a batch of iron-carbohydrate complexes having an effective bioequivalence for administering to a subject, comprising:

formulating a batch of iron-carbohydrate complexes;

contacting the complexes with a reducing agent;

determining a $T_{75}$ for the reduction kinetics of the complexes wherein a $T_{75}$ of less than about 20 minutes indicates that the batch of iron-carbohydrate complexes has an effective bioequivalence when administered to a subject.

11. A quality control method according to claim 10, wherein the carbohydrate of the iron-carbohydrate complexes comprises at least one member selected from the group consisting of dextran, dextrin, gluconate, sorbitol and sucrose.

12. A quality control method according to claim 11, wherein the carbohydrate comprises sucrose.

13. A method of assessing bioequivalence of iron colloids in an iron-carbohydrate complex for administering to a subject, comprising:

contacting the complex with a reducing agent;

measuring the concentration of trivalent iron colloids over a period of time; and obtaining a reduction reaction plot of Log(% trivalent iron colloid concentration) versus time, wherein a plot having an absolute linear regression with a correlation coefficient of not less than 0.98 indicates an effective bioequivalence of iron colloids in the complex when administered to a subject.

14. A quality control to identify a batch of iron-carbohydrate complexes having an effective bioequivalence for administering to a subject, comprising the steps of:

formulating a batch of iron-carbohydrate complexes;

contacting the complexes with a reducing agent;

measuring the concentration of trivalent iron colloids over a period of time; and obtaining a reduction reaction plot of Log(% trivalent iron colloid concentration) versus time, when a plot having an absolute linear regression with a correlation coefficient of not less than 0.98 indicates that the batch of iron-carbohydrate complexes has an effective bioequivalence when administered to a subject.

15. The method according to claim 13 or 14, wherein the carbohydrate of the iron-carbohydrate complex comprises at least one member selected from the group consisting of dextran, dextrin, gluconate, sorbitol and sucrose.

16. The method according to claim 15, wherein the carbohydrate comprises sucrose.

17. The method according to claim 10, 13 or 14, wherein the reducing agent comprises at least one member selected from the group consisting of reduced flavin mononucleotide, dithionite, thioglycolate, hydroquinone, lactate, citrate, bicarbonate, pyruvate, succinate, fructose, cysteine, sorbitol, and ascorbic acid.

18. The method according to claim 17, wherein the reducing agent comprises ascorbic acid.

19. The method according to claim 10, 13 or 14, wherein the reducing agent is present in an amount sufficient to drive the reduction of the complex to substantial completion.

20. The method according to claim 10, 13 or 14, wherein the reducing agent is present in at least about a 50-fold excess to the iron-carbohydrate complex.

21. The method according to claim 10, 13 or 14, wherein the reducing agent is in solution and has an acidic pH.

22. The method according to claim 21, wherein the solution has a pH of from about 1.0 to about 4.0.

23. The method of claim 10 or 14, wherein formulating the batch of iron-carbohydrate complexes comprises:

contacting a saturated ferric ion solution with an alkali to obtain colloidal ferric hydroxide gel;

washing the gel with water to remove any by-product; and adding saturated sucrose solution to the washed gel.

24. The method of claim 10 or 14, wherein formulating the batch of iron-carbohydrate complexes comprises:

contacting a saturated ferric chloride solution with a sodium carbonate solution to obtain colloidal ferric hydroxide gel;

washing the gel with water to remove sodium chloride;

adding saturated sucrose solution to the washed gel to obtain a final elemental iron concentration of about 20 mg/ml;

adjusting the pH to about 10.7; and mixing the solution at about 90° C. for about 3 hours.

25. The method of claim 24, wherein the sodium carbonate solution is 10% w/v sodium carbonate solution.

* * * * *